(12) United States Patent
Chida et al.

(10) Patent No.: US 8,943,909 B2
(45) Date of Patent: Feb. 3, 2015

(54) AUTOMATIC ANALYZER

(75) Inventors: Satoru Chida, Hitachinaka (JP);
Hirokazu Iwamatsu, Hitachinaka (JP);
Kano Shimizu, Hitachinaka (JP);
Kazuhiro Nakamura, Naka (JP);
Kiyotaka Umino, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 112 days.

(21) Appl. No.: 13/264,996

(22) PCT Filed: Apr. 7, 2010

(86) PCT No.: PCT/JP2010/002526
§ 371 (c)(1),
(2), (4) Date: Nov. 3, 2011

(87) PCT Pub. No.: WO2010/122718
PCT Pub. Date: Oct. 28, 2010

(65) Prior Publication Data
US 2012/0036944 A1 Feb. 16, 2012

(30) Foreign Application Priority Data
Apr. 20, 2009 (JP) .................................. 2009-101528

(51) Int. Cl.
*G01N 1/22* (2006.01)
*G01N 35/02* (2006.01)
(Continued)

(52) U.S. Cl.
CPC ........ *G01N 35/026* (2013.01); *G01N 35/00613* (2013.01); *G01N 35/00732* (2013.01); *G01N 2035/0465* (2013.01)
USPC ....................................................... 73/863.01

(58) Field of Classification Search
USPC ..................... 73/863.01; 435/7.1, 40.52, 40.5
See application file for complete search history.

(56) References Cited

U.S. PATENT DOCUMENTS 6,592,822 B1 * 7/2003 Chandler ................... 422/82.05
6,629,060 B2 * 9/2003 Okuno et al. ................. 702/187
(Continued)

FOREIGN PATENT DOCUMENTS

JP 2000-46835 A 2/2000
JP 2000-88861 A 3/2000
(Continued)

OTHER PUBLICATIONS

Japanese Office Action received in Japanese Application No. 2011-510164 dated Jun. 24, 2014.

*Primary Examiner* — Hezron E Williams
*Assistant Examiner* — Mark A Shabman
(74) *Attorney, Agent, or Firm* — Mattingly & Malur, PC

(57) ABSTRACT

The present invention provides an automatic analyzer, in which when a specimen that cannot be analyzed due to an abnormality or needs to be remeasured exists, the automatic analyzer can swiftly reload the specimen that cannot be analyzed due to the abnormality or needs to be remeasured without waiting for completion of a measurement of another specimen held by a rack holding the specimen that cannot be analyzed or needs to be remeasured. The automatic analyzer has means for storing information of a rack loaded in the analyzer and specimen information, displaying identification information of the rack loaded in the analyzer to a user, specifying a specimen that needs to be reanalyzed due to an abnormality or needs to be collected for a remeasurement, interrupting analysis of a specimen rack holding the specimen, and collecting the specimen rack. The automatic analyzer can collect and reload the specified specimen.

16 Claims, 11 Drawing Sheets

(51) Int. Cl.
 *G01N 35/00* (2006.01)
 *G01N 35/04* (2006.01)

(56) References Cited

U.S. PATENT DOCUMENTS

| | | | |
|---|---|---|---|
| 6,733,987 B2 * | 5/2004 | Ogawa et al. | 435/40.52 |
| 6,937,964 B2 * | 8/2005 | Okuno et al. | 702/187 |
| 7,403,873 B2 * | 7/2008 | Okuno et al. | 702/187 |
| 8,043,561 B2 * | 10/2011 | Yamakawa et al. | 422/65 |
| 2002/0142412 A1 * | 10/2002 | Ogawa et al. | 435/173.1 |
| 2004/0037679 A1 | 2/2004 | Sato et al. | |
| 2005/0136509 A1 * | 6/2005 | Gholap et al. | 435/40.5 |
| 2005/0177345 A1 * | 8/2005 | Okuno et al. | 702/187 |
| 2008/0219887 A1 * | 9/2008 | Akutsu | 422/67 |
| 2008/0234945 A1 * | 9/2008 | Walk et al. | 702/19 |
| 2009/0162862 A1 * | 6/2009 | Merz | 435/6 |
| 2009/0223308 A1 * | 9/2009 | Fukuma | 73/863.01 |
| 2009/0305392 A1 * | 12/2009 | Alfredsson et al. | 435/286.1 |
| 2010/0031757 A1 * | 2/2010 | Hoyer | 73/863.01 |
| 2011/0256022 A1 * | 10/2011 | Akutsu et al. | 422/65 |

FOREIGN PATENT DOCUMENTS

| | | |
|---|---|---|
| JP | 2001-4639 A | 1/2001 |
| JP | 2002-323506 A | 11/2002 |
| JP | 2003-083991 A | 3/2003 |
| JP | 2004-061169 A | 2/2004 |
| JP | 2004-075363 A | 3/2004 |

* cited by examiner

FIG. 10

STORAGE TRAY STATUS SCREEN

Tray
| | 1 2 3 4 5 | |
|---|---|---|
| N00001 | ⊚⊚⊚⊗⊚ | ! —1011 |
| N00002 | ⊚⊚⊚⊚⊚ | |
| N00003 | ⊚⊗⊚⊚⊚ | ! |
| N00004 | ⊚⊗⊚⊚⊚ | ! |
| N00005 | ⊚⊚⊚⊚⊚ | |
| N00006 | ⊗⊗⊗⊗⊗ | ! |
| N00007 | ⊗⊗⊗⊗⊗ | ! |
| N00008 | ⊚⊚⊚⊚⊚ | |
| N00009 | ⊚⊚⊚⊚⊚ | |
| N00010 | ⊚⊚⊚⊚⊚ | |

1001   1002

1003 — Rack Information
N00001 ⊚⊚⊚⊗⊚ —1004

| S.NO. | Sample ID | Comment |
|---|---|---|
| 1 | 00001 | 000000001 | ABCDEFG |
| 2 | 00002 | 000000002 | ABCDEFG |
| 3 | 00003 | 000000003 | ABCDEFG |
| 4 | 00004 | 000000004 | ABCDEFG |
| 5 | 00005 | 000000005 | ABCDEFG |

1005   1006   1007

Position Status
⊚ Complete   ⊗ Not Processed

Cancel —1009        1008   OK —1010

AUTOMATIC ANALYZER

TECHNICAL FIELD

The present invention relates to an automatic analyzer that quantitatively and qualitatively analyzes biological samples such as blood or urine, and more particularly to an automatic analyzer having a transport device for transporting sample vessels to an analyzing device.

BACKGROUND ART

Automatic analyzers automatically perform quantitative and qualitative analysis on biological samples such as blood and urine. Those automatic analyzers are prevailing mainly in large hospitals and clinical inspection centers, where a large number of patients' specimens are required to be processed within limited time. According to the throughputs, long, medium and small-sized automatic analyzers are being developed. In a large automatic analyzer that performs a process of analyzing a large number of specimens per unit of time, specimen vessels that store specimens are held by a holder, called specimen rack, and the specimen vessels are transported to a plurality of analyzing devices through a transport line (transport device). The automatic analyzer outputs an analysis result automatically only if a laboratory technician loads a rack in a specimen rack loading port.

In this case, the specimen rack loaded in the specimen rack loading port is transported through a belt-conveyor-like transport line, during which a barcode reader installed above the transport line reads and recognizes the type of the rack and a specimen for analysis.

It is requested that automatic analyzers output measurement results as fast as possible in the facilities where a large number of patients' specimens are processed daily.

Meanwhile, in the large automatic analyzer or a specimen pretreatment device that performs a pretreatment such as centrifugal separation on a sample in order to enable the automatic analyzer to analyze the sample, an analysis or treatment could fail for some reason. For example, a dispensing nozzle becomes clogged during dispensing a sample in some cases, or an identification (ID) attached to a rack or a sample vessel is not successfully read in some cases are conceivable as the reasons. Patent Document 1 discloses a specimen pretreatment device for pretreatment such as centrifugal separation on a blood sample, the known specimen pretreatment device extracts, at the time of a failure of the pretreatment, a rack on which the pretreatment has not be completed, and places the rack in a rack extraction port. With this device, the interrupted treatment can be completed by placing the rack from the rack extraction port to a rack supply unit by an operator.

PRIOR-ART DOCUMENTS

Patent Document

Patent Document 1: JP-2000-88861-A

SUMMARY OF THE INVENTION

Problems to be Solved by the Invention

In the specimen pretreatment device disclosed in Patent Document 1, even a failed sample suspends the process for other samples without failure because the device extracts the failed sample held by a specimen rack unconditionally to the rack extraction port. On the other hand, a large automatic analyzer including a rack transport mechanism differs from the above-mentioned specimen pretreatment device in that the automatic analyzer carries on measurements patients' specimens. With a rack is loaded with a plurality of patients' specimens, the automatic analyzer thus carries on measurements even the analyzer fails to read ID information of a specimen which specifies the patient's specimen. The automatic analyzer cannot collect the rack measurements of the other patients' specimens are completed. As a result, in order to measure the specimen whose ID information has failed to be read, the specimen needs to be reloaded after the rack holding the specimen is collected in a rack collecting port.

In addition, the aforementioned problem occurs even when a sample shortage of a single specimen is detected. Furthermore, when a request to measure a certain specimen is insufficient, the specimen needs to be immediately collected and reloaded, leading to the aforementioned problem.

An object of the present invention is to provide an automatic analyzer that can swiftly remeasure a patient's specimen even when a reading error of the patient's specimen ID, an abnormality disabling analysis due to a lack of the sample and the like, or a request to measure the specimen is insufficient occurs.

Means for Solving the Problems

In order to reach the aforementioned object, the present invention configures as follows.

An automatic analyzer includes: an analyzing mechanism adapted to analyze a biological sample; a sample transport device adapted to transport the biological sample to the analyzing mechanism; a sample loading port adapted to load the biological sample onto the sample transport device; a sample collecting port adapted to collect the sample so that the sample can be extracted; and a control mechanism adapted to control the sample transport device so that the sample that is specified is collected by the sample collecting port.

The analyzing mechanism may be physically divided into analyzing units or may be a single inseparable unit. Any types of sample transport devices are applicable as long as the sample transport device has a function of transporting the sample. The sample transport device may be a so-called belt conveyor provided with a belt on which the sample is placed and is moved by the belt conveyor. Further, the sample transport device may have a pushing nail that pushes the sample. The sample may either be held in a sample vessel or be held by a so-called specimen rack that can hold one or more sample vessels. It is preferable that the automatic analyzer includes specifying means for specifying a sample wherein preferably, the specifying means displays a list of samples that can be specified on a screen, specifies an arbitrary sample among the displayed samples.

Effects of the Invention

The present invention can provide the specimen processing system wherein a specimen that needs to be reanalyzed or reloaded due to an abnormality can be specified, analysis of a rack holding the specimen can be interrupted and the rack loaded with the arbitrary specimen can be collected. Thus, a user can reconfirm the state of the specimen necessary to be reanalyzed and reload the specimen without waiting for analysis of other specimens held by the same rack to be completed. Therefore, the specimen processing system can swiftly obtain a measurement result.

BRIEF DESCRIPTION OF THE DRAWINGS

FIG. 10 is an explanatory diagram illustrating means for displaying specimen rack information stored in a storage tray according to the embodiment of the present invention.

MODE FOR CARRYING OUT THE INVENTION

The configuration and operations of an automatic analyzing system according to an embodiment of the present invention are described with reference to the accompanying drawings.

Figure 1:
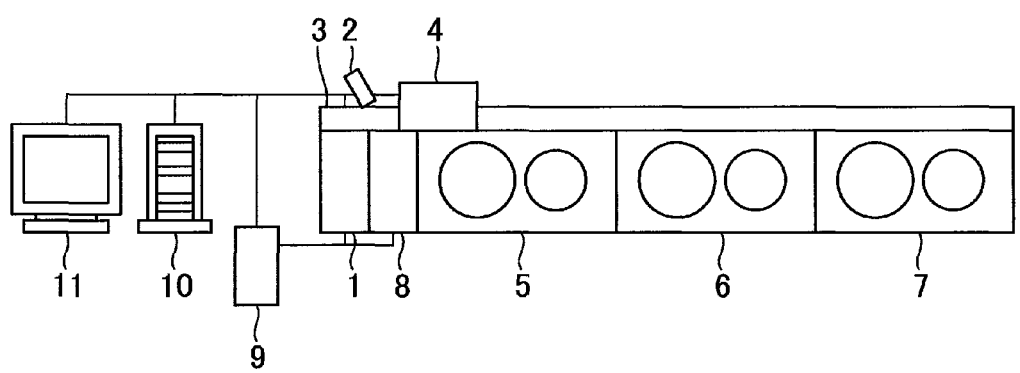
FIG. 1 is a system block diagram illustrating the whole configuration of an automatic analyzer according to an embodiment of the present invention.

FIG. 1 is an outline diagram illustrating the whole configuration of an automatic analyzer according to the embodiment of the present invention.

The automatic analyzing system according to the present embodiment includes a specimen rack loading unit 1, an ID reader 2, a transport line 3, a specimen rack standby unit 4, analyzing modules 5, 6 and 7, a specimen rack collecting unit 8, a whole management computer 9.

The specimen rack loading unit 1 is a unit that loads a plurality of specimen racks that each holds a plurality of specimens (samples). The analyzing modules 5, 6 and 7 are arranged along the transport line 3 and connected to the transport line 3 so that the analyzing modules 5, 6 and 7 are detachable from the transport line 3. The number of analyzing modules can be set arbitrarily. The present embodiment describes the case in which the three analyzing modules are provided.

The transport line 3 transports a specimen rack from the specimen rack loading unit 1 to the analyzing modules 5, 6 and 7 in accordance with an analysis request. The transport line 3 also transports a specimen rack analyzed by the analyzing modules 5, 6 and 7 to the specimen rack standby unit 4, which is held in the transport line 3. The transport line 3 transports, to the specimen rack collecting unit 8, a specimen rack which is not provided an analysis request.

The specimen rack standby unit 4 is installed on the transport line 3 that transports a rack holding a standard specimen, an accuracy management sample and a general specimen. The specimen rack standby unit 4 is a line mechanism capable of holding one or more specimen racks. The specimen rack standby unit 4 is capable of holding, for an arbitrary time, a rack holding an arbitrary sample to be transported by the transport line 3 and resupplying the rack to the analyzing modules or the specimen rack collecting unit 8 at an arbitrary timing.

The specimen rack loading unit 1 has the whole management computer 9. The whole management computer 9 performs control that is necessary for the specimen rack loading unit 1, the ID reader 2, the transport line 3, the specimen rack standby unit 4 and the specimen rack collecting unit 8. The whole management computer 9 is further connected to an operating unit 10 and a display unit 11, whereby inputs necessary information and displays an analysis result, respectively.

A specimen held by a specimen rack has a specimen ID that indicates attribute information (a reception number, a patient's name, a requested analysis item and the like) relating to the specimen. In addition, the specimen rack has a rack ID that indicates rack identification information such as a rack number. The specimen rack that is placed on the specimen rack loading unit 1 is transported by the transport line 3. Upon the specimen rack is loaded on the transport line 3, the specimen ID and the specimen rack ID are read by the ID reader 2 and transmitted to the whole management computer 9. The whole management computer 9 determines, based on the requested analysis item of the attribute information, an analyzing module that performs analysis with.

At this time, the whole management computer 9 conducts matching of the specimen with rack collection request information stored in a storage device included in the whole management computer 9, and activates a rack transport scheduler.

When the rack starts to be transported, the rack transport scheduler conducts matching of the rack with the rack collection request information stored in the storage device included in the whole management computer 9, automatic collection information, and rack transport status information. When the rack matches the collection request information or the rack transport status information, the rack transport scheduler interrupts the transport of the rack to an analysis module scheduled to analyze the rack. Then the rack transport scheduler generates a rack collection schedule to collect the rack.

When the rack does not match any of the rack collection request information, the automatic collection information and the rack transport status information, the rack transport scheduler generates a rack transport schedule for transport the rack to the analyzing module scheduled to analyze the rack to transport the rack.

The rack collection request information is information stored in the storage device included in the whole management computer 9 and indicating a rack instructed by a user to be collected.

The automatic collection information is information stored in the storage device included in the whole management computer 9 and specifying; the interruption of analysis the rack upon detecting an abnormality; and immediate collection of the rack.

The rack transport status information is information also stored in the storage device included in the whole management computer 9. The rack transport status information is generated from a report provided at the time of transporting a rack from the specimen rack loading unit 1, the ID reader 2, the transport line 3, the specimen rack standby unit 4, the analyzing modules 5, 6, 7 or the specimen rack collecting unit 8. The rack transport status information is also generated from a report of analysis progress.

Next, a process of determining a specimen rack transport schedule in the automatic analyzing system according to the present embodiment is described with reference to FIGS. 2 and 3.

Figure 2:
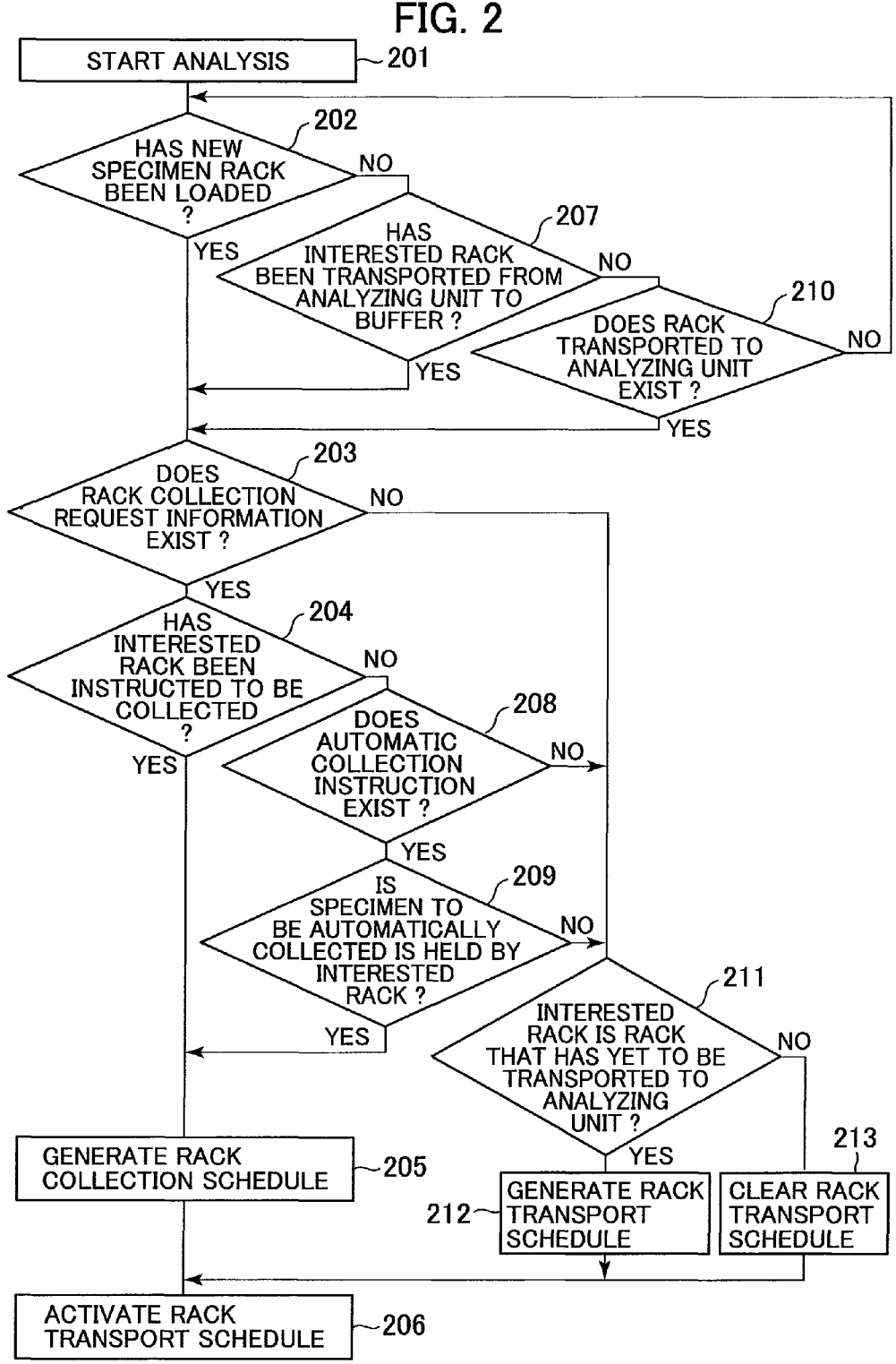
FIG. 2 is a flowchart illustrating procedures of operations for the automatic analyzing system according to the embodiment of the present invention.

FIG. 2 is a flowchart of the process of determining a specimen rack transport schedule in the automatic analyzing system according to the embodiment of the present invention.

Figure 3:
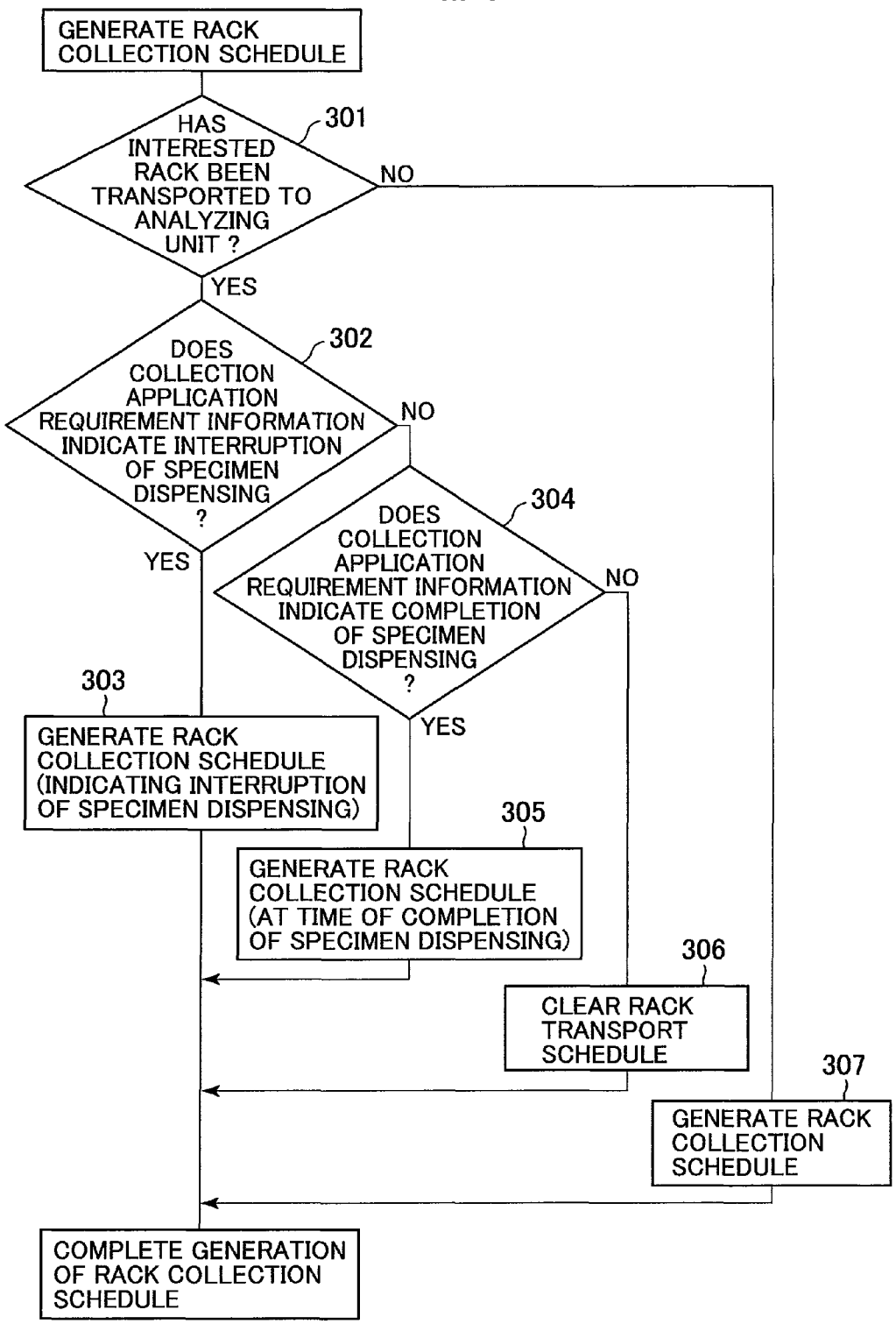
FIG. 3 is a flowchart illustrating procedures to determine a rack collection schedule for the automatic analyzing system according to the embodiment of the present invention.

FIG. 3 is a flowchart of a process of determining a rack collection schedule in the process of determining a specimen rack transport schedule in the automatic analyzing system according to the embodiment of the present invention.

In step 201, receives a request to start analysis from the operating unit 10 and the display unit 11 and the whole management computer 9 instructs to start analysis the analyzing modules 5, 6 and 7 so that the whole state of the automatic analyzer is analyzing.

In step 202, a rack is determined whether or not the rack is loaded by the specimen rack loading unit 1, and when the rack is determined that loaded by the specimen rack loading unit 1, the process proceeds to step 203.

When the rack is not determined that loaded by the specimen rack loading unit 1, the process proceeds to step 207.

In step 203, it is determined whether or not the rack collection request information stored in the storage device included in the whole management computer 9.

When the determination result indicates "Yes" that the rack collection request information is stored, the process proceeds to step 204.

When the determination result indicates "No" that the rack collection request information is not stored, the process proceeds to step 211.

In step 204, it is determined whether or not the rack collection request information stored in the storage device included in the whole management computer 9 matches the rack.

When the matching result indicates "Yes" that the rack collection request information matches the rack, the process proceeds to step 205.

When the matching result indicates "No" that the rack collection request information does not match the rack, the process proceeds to step 208.

In step 205, a rack collection schedule is generated for the rack.

The process of determining the rack collection schedule is described below with reference to FIG. 3.

In step 301, referring to the rack transport status information stored in the storage device included in the whole management computer 9, and matching is conducted to determine whether or not the rack is a rack transported to an analyzing unit.

When the matching result indicates "Yes" that the rack is the rack transported to the analyzing unit, the process proceeds to step 302.

When the matching result indicates "No" that the rack is not the rack transported to the analyzing unit, the process proceeds to step 307.

In step 302, it is determined whether or not collection application condition information stored in the storage device included in the whole management computer 9 indicates an "interruption of specimen dispensing."

When the collection application condition information indicates "Yes" that the "interruption of specimen dispensing," the process proceeds to step 303.

When the collection application condition information indicates "No" that the "interruption of specimen dispensing," the process proceeds to step 304.

In step 303, the rack transport schedule for the rack is set to "interruption of specimen dispensing and collection of the rack into the rack collecting unit 8."

In step 304, it is determined whether or not the collection application condition information stored in the storage device included in the whole management computer 9 indicates "completion of specimen dispensing."

When the collection application condition information indicates "Yes" or "completion of specimen dispensing," the process proceeds to step 305.

When the collection application condition information indicates "No" or "completion of specimen dispensing," the process proceeds to step 306.

In step 305, the rack transport schedule for the rack is set to "collection of the rack into the rack collection unit 8 after completion of specimen dispensing."

In step 306, the rack transport schedule for the rack is set to "no schedule."

In step 307, the rack transport schedule for the rack is set to "collection of the rack into the rack collecting unit 8."

In step 206, the transport schedule determined for the rack is activated in order for the rack to be collected by the rack collecting unit 8.

In step 207, referring to the rack transport status information stored in the storage device included in the whole management computer 9, matching is conducted to determine whether or not the rack is a rack transported from any of the analyzing modules 5, 6 and 7 to the specimen rack standby unit 4.

When the matching result indicates "Yes" that the rack is the rack transported to the specimen rack standby unit 4, the process proceeds to step 203.

When the matching result indicates "No" that the rack is not the rack transported to the specimen rack standby unit 4, the process proceeds to step 210.

In step 208, it is determined whether or not the automatic collection information that is stored in the storage device included in the whole management computer 9 indicates that an automatic collection instruction exists.

When the automatic collection information indicates "Yes" or "the automatic collection instruction exists," the process proceeds to step 209.

When the automatic collection information indicates "No" or "the automatic collection instruction does not exist," the process proceeds to step 211.

In step 209, alarm information, that is added to a measurement result of a specimen held by the rack stored in the storage device included in the whole management computer 9 with the automatic collection information stored in the storage device included in the whole management computer 9. Thereby it is determined whether or not the specimen held by the rack is subject to collection.

When the matching result indicates "Yes" that the alarm information matches the automatic collection information, it is determined that the specimen held by the rack is subject to collection, and the process proceeds to step 205.

When the matching result indicates "No" that the alarm information does not match the automatic collection information, it is determined that the specimen held by the rack is not subject to collection, and the process proceeds to step 211.

In step 210, referring to the rack transport status information stored in the storage device included in the whole management computer 9, matching is conducted to determine whether or not the rack is already transported to the analyzing modules 5, 6 and 7.

When the matching result indicates "Yes" that the rack is already transported to the analyzing modules 5, 6 and 7, the process proceeds to step 203.

When the matching result indicates "No" that the rack is not transported to the analyzing modules 5, 6 and 7, the process proceeds to step 202.

In step 211, referring to the rack transport status information that is stored in the storage device included in the whole management computer 9, matching is conducted to determine whether or not the rack is a rack that has yet to be transported to the analyzing modules 5, 6 and 7.

When the matching result indicates "Yes" that the rack is the rack that has yet to be transported to the analyzing modules 5, 6 and 7, the process proceeds to step 212.

When the matching result indicates "No" that the rack is not the rack that has yet to be transported to the analyzing modules 5, 6 and 7, the process proceeds to step 213.

In step 212, matching is conducted to determine whether or not the rack matches the analysis request information stored in the storage device included in the whole management computer 9, an analyzing module to which the rack is to be transported is specified, and a rack transport schedule is set.

In step 213, the rack transport schedule for the rack is set to "no schedule."

Next, a process of searching a specimen that cannot be analyzed or needs to be remeasured in the automatic analyzing system according to the present embodiment is described with reference to FIG. 4.

Figure 4:
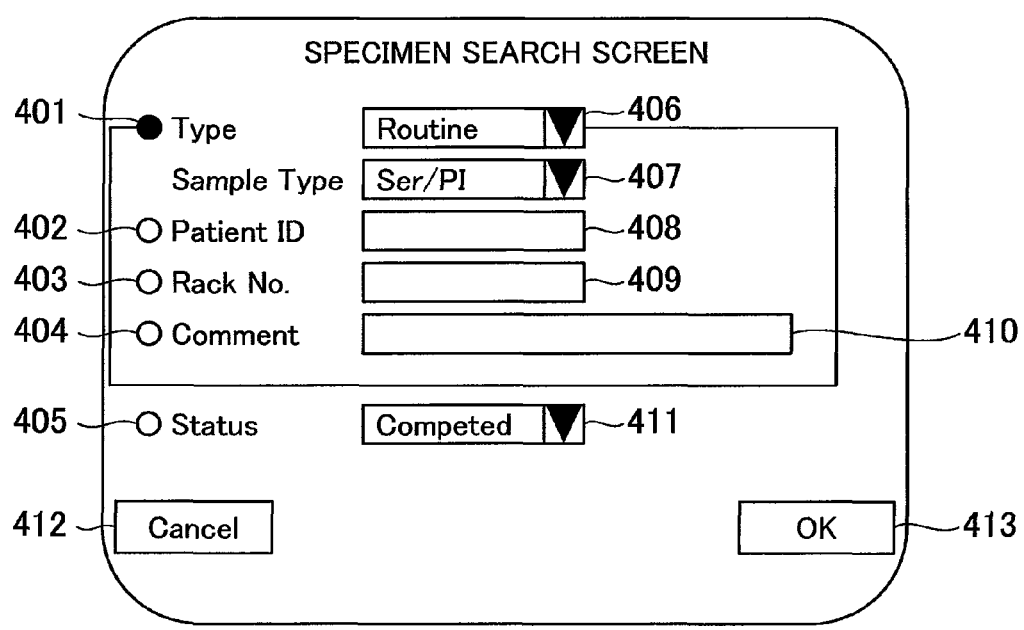
FIG. 4 is an explanatory diagram illustrating means for searching a specimen that cannot be reanalyzed or needs to be remeasured according to the embodiment of the present invention.

FIG. 4 is a diagram illustrating means for searching a specimen that cannot be analyzed or needs to be remeasured according to the present embodiment.

A specimen search button 401 or an analysis status search button 405 is selected, and key information to be searched is set.

When the specimen search button 401 is selected, a specimen type is selected by using a specimen type select button 406. Further, a specimen type is selected by using a specimen type select button 407.

After that, key information to be used for search is selected from among a specimen ID button 402, a rack number button 403 and a comment button 404.

When the specimen ID button 402 is selected in accordance with the selected search key information, a specimen ID to be searched is entered in a specimen ID entry box 408.

When the rack number button 403 is selected, a rack number is entered in a rack number entry box 409.

When the comment button 404 is selected, specimen comment information to be searched is entered in a comment entry box 410.

After that, when an OK button 413 is pressed, matching is conducted to determine whether or not the specified specimen information matches specimen information included in the rack transport status information stored in the storage device included in the whole management computer 9, and matched specimen rack information is displayed.

When a cancel button 412 is pressed, the specimen search is not performed, and a screen is closed.

When the analysis status search button 405 is selected, an analysis status is selected using an analysis status select button 411.

After that, when the OK button 413 is pressed, matching is conducted to determine whether or not the selected analysis status matches an analysis status included in the rack transport status information stored in the storage device included in the whole management computer 9, and matched specimen rack information is displayed.

As described above, since a plurality of specimen search conditions are prepared so that a condition can be selected from among the specimen search conditions. Thus, the user can select a search condition according to an operation state.

Next, a process of displaying a search result of a specimen that cannot be analyzed or needs to be remeasured in the automatic analyzing system according to the present embodiment as well as a process of instructing rack collection are described with reference to FIGS. 5, 6 and 7.

Figure 5:
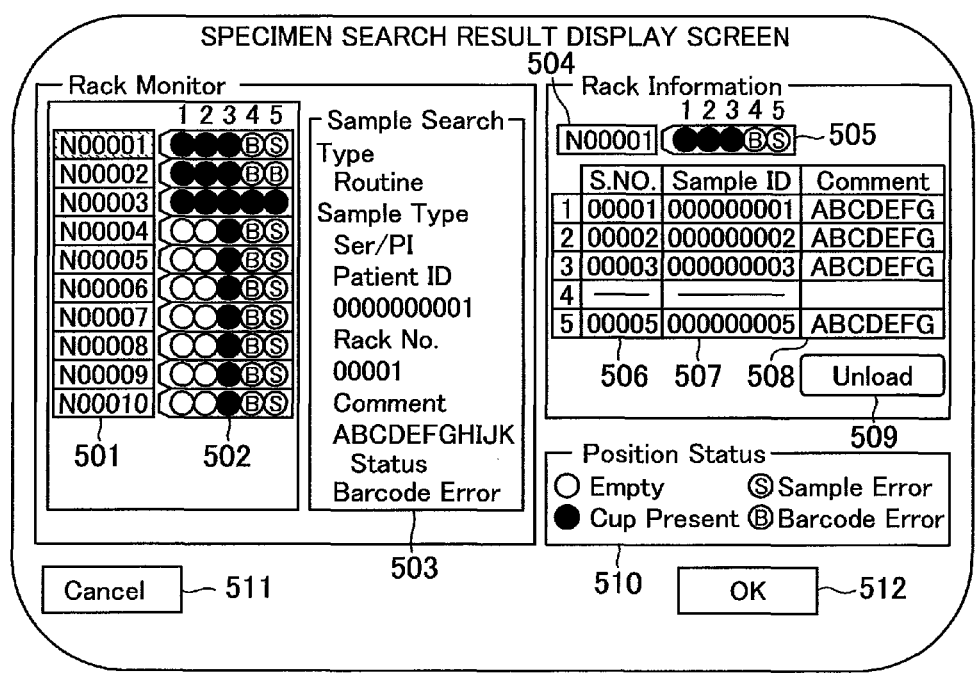
FIG. 5 is an explanatory diagram illustrating means for displaying a searching result of the specimen that cannot be reanalyzed or needs to be remeasured, and for issuing an instruction to collect a rack according to the embodiment of the present invention.

FIG. 5 is a diagram illustrating means for displaying a search result of a specimen that cannot be analyzed or needs to be remeasured and an instruction to collect a rack according to the embodiment of the present invention.

Figure 6:
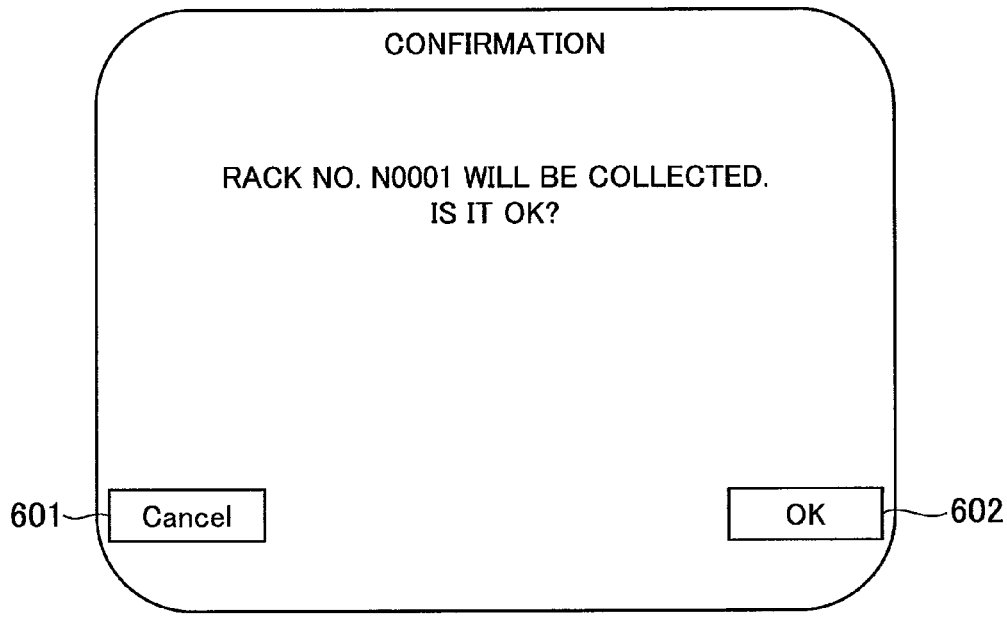
FIG. 6 is an explanatory diagram illustrating means for executing a confirmation when the rack collection instruction is issued according to the embodiment of the present invention.

FIG. 6 is a diagram illustrating means for executing a confirmation when an instruction to collect a rack is issued according to the embodiment of the present invention.

Figure 7:
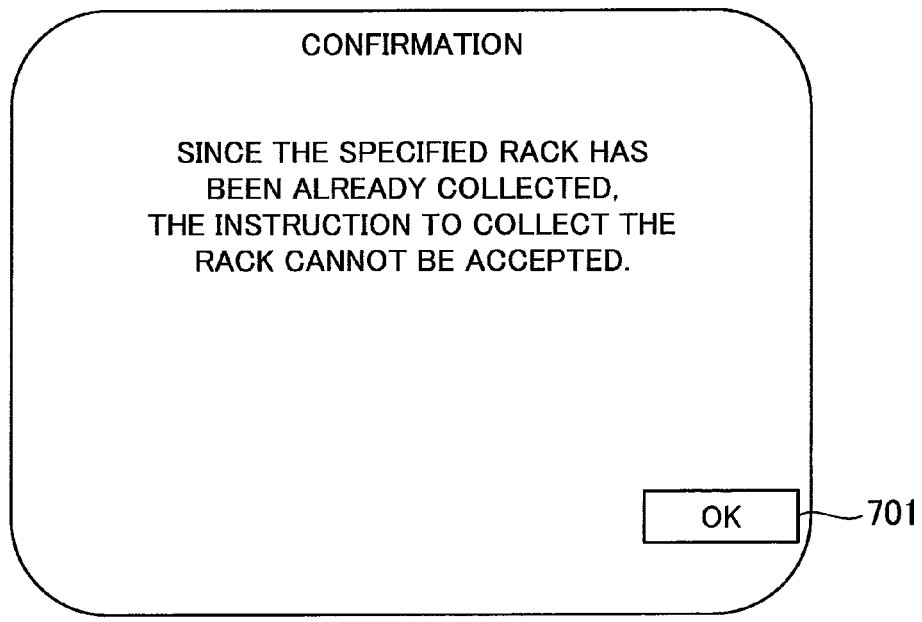
FIG. 7 is an explanatory diagram illustrating means for informing a user the reason that a rack cannot be collected when the rack collection instruction is issued according to the embodiment of the present invention.

FIG. 7 is a diagram illustrating means for informing the user of a reason that the rack correction cannot be executed, when the rack collection instruction is issued according to the embodiment of the present invention.

The result (described with reference to FIG. 4) of searching the specimen, and specimen rack information that corresponds to the selected search key information, are displayed as a list on a screen.

A rack number is displayed in a rack number select button 501. When the rack number select button 501 is pressed, information on the selected rack is displayed in a specimen placement status display box 505, a specimen number display box 506, a specimen ID display box 507 and a specimen comment display box 508.

The analysis status of a specimen held by the rack is displayed in the specimen placement status display box 502.

A predicted time when the rack is stored in a specimen rack storage unit after completion of the analysis of the rack is displayed in a predicted collection time display box 513. Thus, the user can determine whether or not the analysis of the rack needs to be interrupted and collected.

When a rack collect button 509 is pressed, a confirmation screen illustrated in FIG. 6 is displayed. When an OK button 602 is pressed, a request to collect the rack currently selected by using the rack number select button 501 is issued to the whole management computer 9.

The whole management computer 9 conducts matching of the rack transport status information stored in the storage device included in the whole management computer 9 with information of the rack requested to be collected, and determines whether or not the request can be accepted.

When the request can be accepted as a result of the determination, the whole management computer 9 stores, as rack collection request information, the information in the storage device included in the whole management computer 9. The user can confirm that the request is accepted by changing a color of the displayed rack number select button 501.

When the request cannot be accepted, the whole management computer 9 notifies the operating unit 10 that the request cannot be accepted.

When the operating unit 10 receives the notification indicating that the request cannot be accepted, the display unit 11 displays a screen (illustrated in FIG. 7) showing that the request cannot be accepted.

When an OK button 701 illustrated in FIG. 7 is pressed, the screen showing that the request cannot be accepted is closed.

When a cancel button 601 is pressed, the rack collection request information is not stored and the confirmation screen is closed.

Next, a process of setting whether to collect a rack holding a specimen that needs to be reloaded according to the present embodiment is described.

Figure 8:
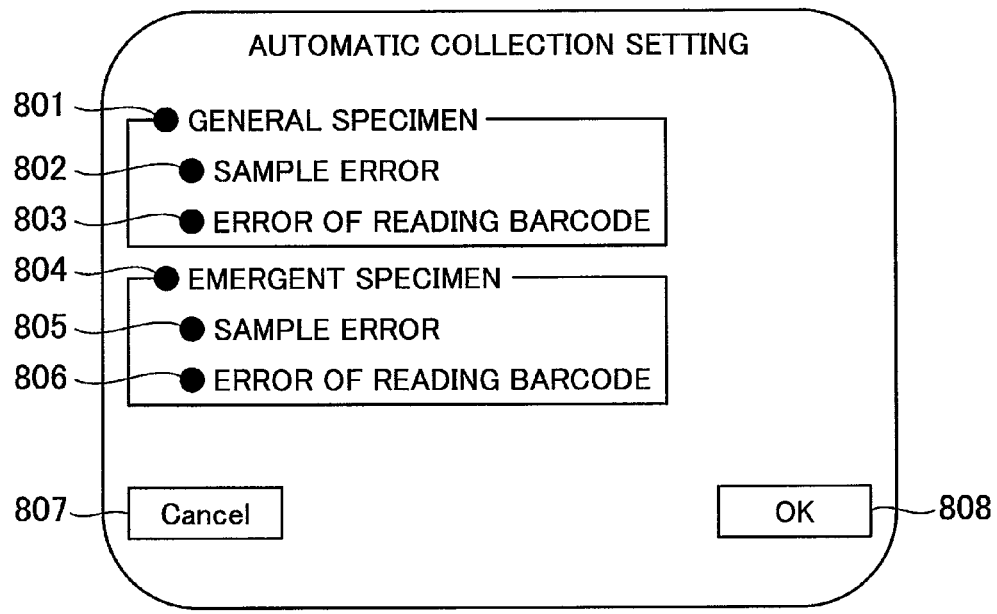
FIG. 8 is an explanatory diagram illustrating means for setting whether to collect a rack holding a specimen that needs to be reloaded according to the embodiment of the present invention.

FIG. 8 is a diagram illustrating means for setting whether to collect a rack holding a specimen that needs to be reloaded according to the embodiment of the present invention.

When a general specimen select button 801 and an emergent specimen select button 804 are pressed, an automatic rack collection is set for each of a general specimen and an emergent specimen.

In addition, when sample error buttons 802, 805 and barcode reading error buttons 803, 806 are pressed, error information is set so that the general specimen and the emergent specimen are subject to automatic rack collection.

Thus, a priority can be set to the emergent specimen of which a measurement result needs to be swiftly output.

When an OK button 808 is pressed, the error information is stored in the automatic collection information stored in the storage device included in the whole management computer 9.

When a cancel button 807 is pressed, the error information is not stored in the storage device included in the whole management computer 9, and the screen is closed.

Next, a process of setting a condition for collecting a specimen rack instructed to be collected is described with reference to FIG. 9.

Figure 9:
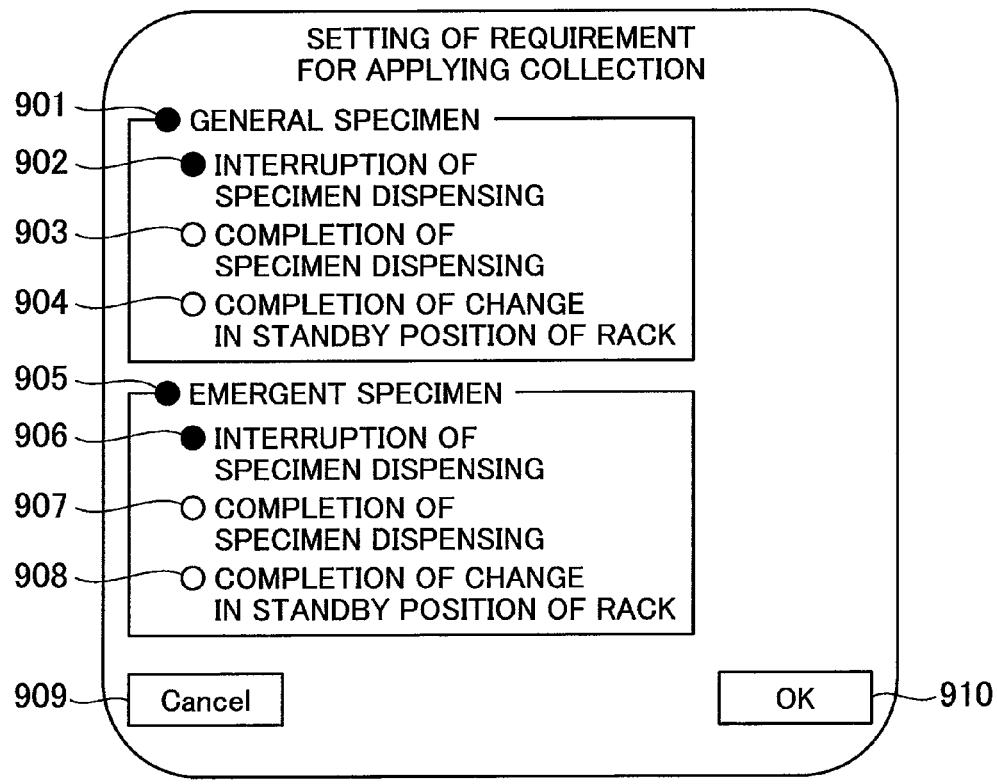
FIG. 9 is an explanatory diagram illustrating means for setting a condition for collecting a specimen rack instructed to be collected according to the embodiment of the present invention.

FIG. 9 is a diagram illustrating means for setting whether to collect a rack holding a specimen needs to be reloaded according to the embodiment of the present invention.

When a general specimen select button 901 is pressed, a condition for applying a collection of a general specimen is set. When an emergent specimen select button 904 is pressed, a condition for applying a collection of an emergent specimen is set.

When the general specimen select button 901 is set to "On," a specimen dispensing interrupt button 902, a specimen dispensing complete button 903 or a rack standby position changing complete button 904 is selected to set a condition for applying an instruction to collect the general specimen.

When the emergent specimen select button 905 is set to "On," a specimen dispensing interrupt button 906, a specimen dispensing complete button 907 or a rack standby position changing complete button 908 is selected to set a condition for applying an instruction to collect the emergent specimen.

When an OK button 910 is pressed, the condition is stored in collection application condition setting information stored in the storage device included in the whole management computer 9.

When a cancel button 909 is pressed, the condition is not stored in the storage device included in the whole management computer 9, and the screen is closed.

Thus, it is possible to select a condition for applying a collection on the basis of the state of an operation performed by the user.

In addition, it is possible to set a priority to an emergent specimen of which a measurement result needs to be swiftly output.

Next, a process of displaying information of a specimen rack stored in the specimen rack storage unit of the automatic analyzing system according to the present embodiment is described with reference to FIG. 10.

FIG. 10 is an explanatory diagram illustrating means for displaying information of a specimen rack stored in the specimen rack storage unit according to the embodiment of the present invention.

A rack number is displayed in a rack number select button 1001. When the rack number select button 1001 is pressed, information of the selected rack is displayed in a specimen placement status display box 1004, a specimen number display box 1003, a specimen ID display box 1006 and a specimen comment display box 1007.

In a rack collection request display box 1011, the rack is stored in the storage tray according to an instruction to collect the rack is displayed and can be identified. In a specimen analysis status display box 1002, the status of analysis of each specimen is displayed so that whether or not the analysis of each specimen has been completed can be identified.

The aforementioned displaying enables information that identifies a specimen rack to be displayed, while the specimen rack holds a specimen that is among samples collected in a sample collecting port according to instructions to collect the samples and needs to be reanalyzed. Thus, it is possible to specify the specimen rack to be reanalyzed.

In a specimen placement status display box 1004, the status of analysis of a specimen held by the rack is displayed.

A specimen collected after the user interrupts analysis can be specified by confirming an analysis status displayed in the specimen placement status display box 1004.

Next, a process of specifying a sample that cannot be analyzed due to an error selected in the error display mechanism of the automatic analyzing system according to the present embodiment is described with reference to FIG. 11.

Figure 11:
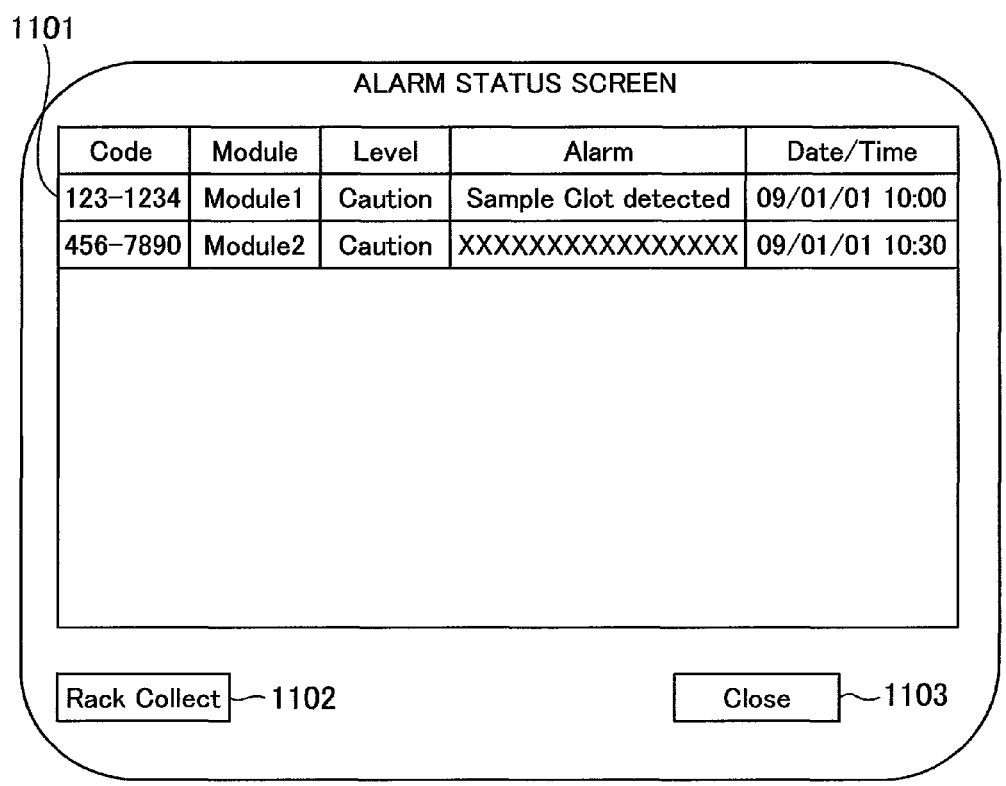
FIG. 11 is an explanatory diagram illustrating means for issuing an instruction to collect a specimen rack holding a specimen that has failed to be analyzed due to an error selected in an error display mechanism according to the embodiment of the present invention.

FIG. 11 is an explanatory diagram illustrating means for issuing an instruction to collect a sample that cannot be analyzed due to an error selected in the error display mechanism according to the embodiment of the present invention.

An error number select button 1101 is selected to specify whether a sample that cannot be analyzed due to an error is present on the basis of error management information and rack transport status information. The storage device included in the whole management computer 9 has, stored therein, the error management information and the rack transport status information.

The error management information is information that is stored in the storage device included in the whole management computer 9 and stores information of an error that has occurred in the automatic analyzer.

When a sample that cannot be analyzed due to the error exists, a rack collect button 1102 is displayed so that the rack collect button 1102 can be pressed.

When a sample that cannot be analyzed due to the error does not exist, the rack collect button 1102 is displayed so that the rack collect button 1102 cannot be pressed.

When the rack collect button 1102 can be pressed and is pressed, the confirmation screen illustrated in FIG. 6 is displayed. When the OK button 602 is pressed, the whole management computer 9 can be instructed to request to collect a sample that cannot be analyzed due to an error currently selected using the error number select button 1101.

Next, means for specifying a sample to be collected by the sample collecting port from a high-order analyzing system connected to an automatic analyzer according to an embodiment is described with reference to FIG. 12.

Figure 12:
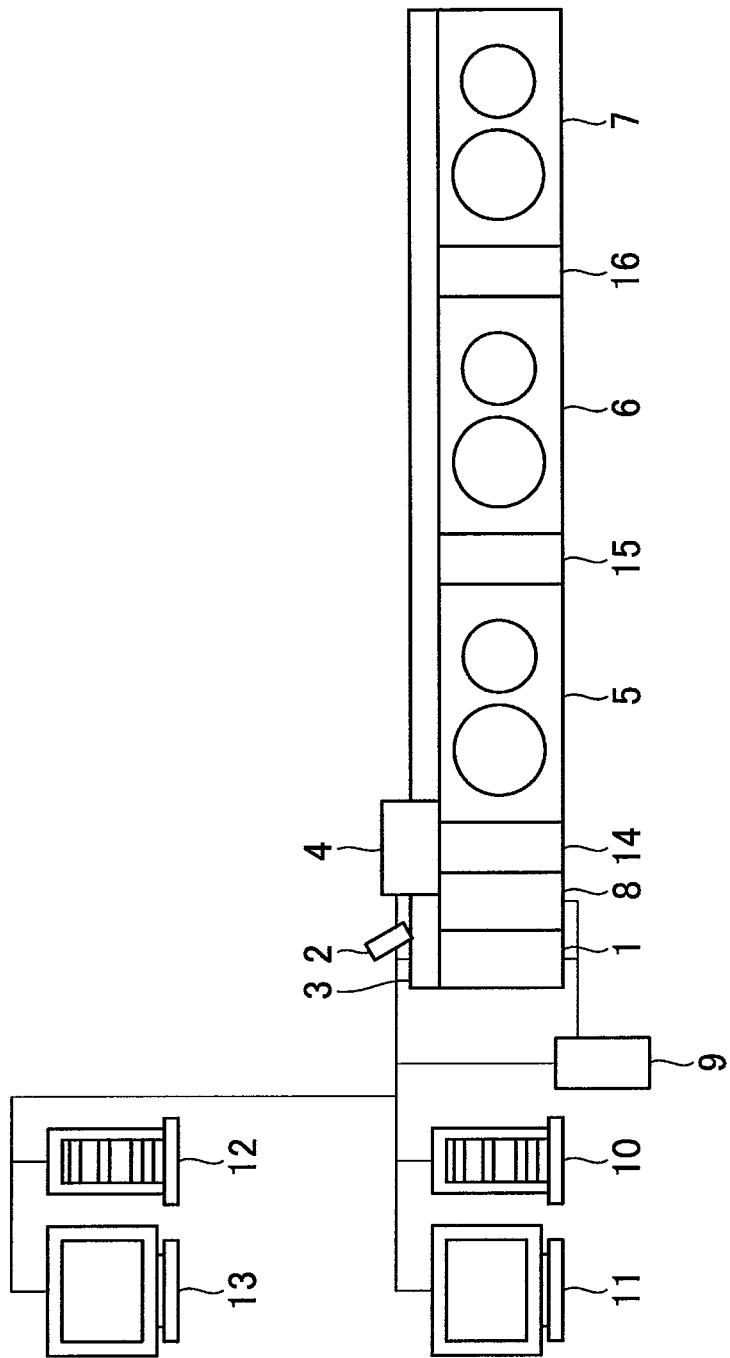
FIG. 12 is a system block diagram illustrating the whole configuration of an automatic analyzer according to the embodiment of the present invention.

FIG. 12 is a diagram illustrating a whole outline structure of the automatic analyzer according to the embodiment of the present invention.

The whole outline structure diagram of FIG. 12 is different from the whole outline structure diagram of FIG. 1 in that the automatic analyzer illustrated in FIG. 12 includes not only the specimen rack collecting unit 8 but for a plurality of specimen rack storage units 14, 15 and 16 connected thereto.

In addition, an operating unit 12 and a display unit 13 are connected to the automatic analyzer. The operating unit 12 is used to enter information necessary for the high-order analyzing system, while the display unit 13 displays the information.

The high-order analyzing system includes operating unit 12 and the display 13 both can enter a searching result for specimen that cannot be analyzed in the automatic analyzing system described with reference to FIGS. 5, 6 and 7 as well as an instruction to collect a rack.

Next, a process of specifying a sample collecting port that collects a specified sample in the automatic analyzing system according to the present embodiment is described with reference to FIGS. 13 and 14.

Figure 13:
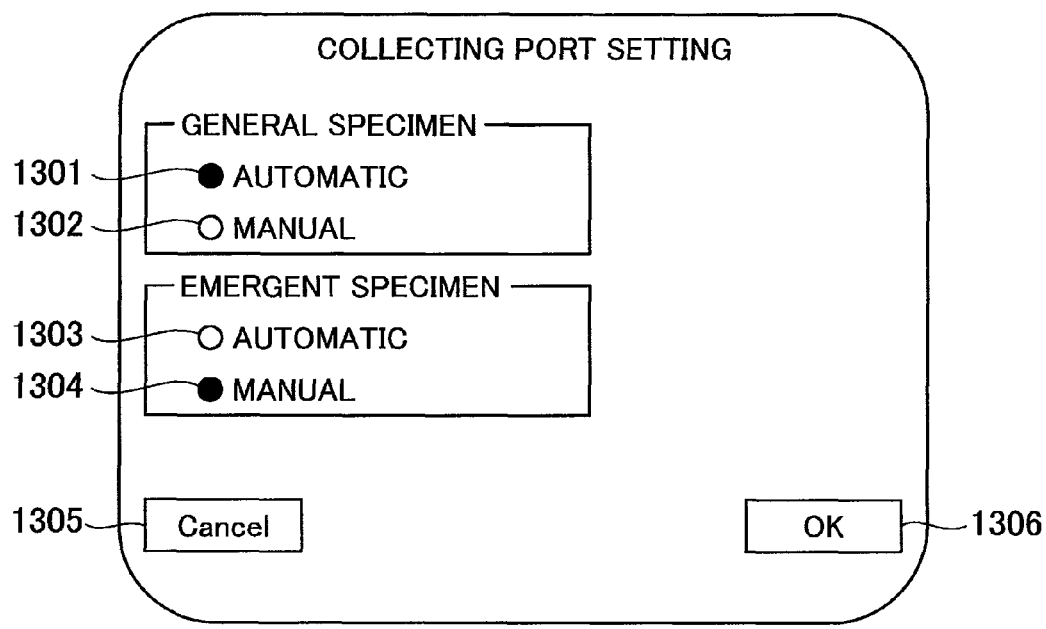
FIG. 13 is an explanatory diagram illustrating means for setting a condition for selecting a sample collecting port according to the embodiment of the present invention.

FIG. 13 is an explanatory diagram illustrating means for setting a condition for specifying a sample collecting port that collects a specified sample according to the embodiment of the present invention.

Figure 14:
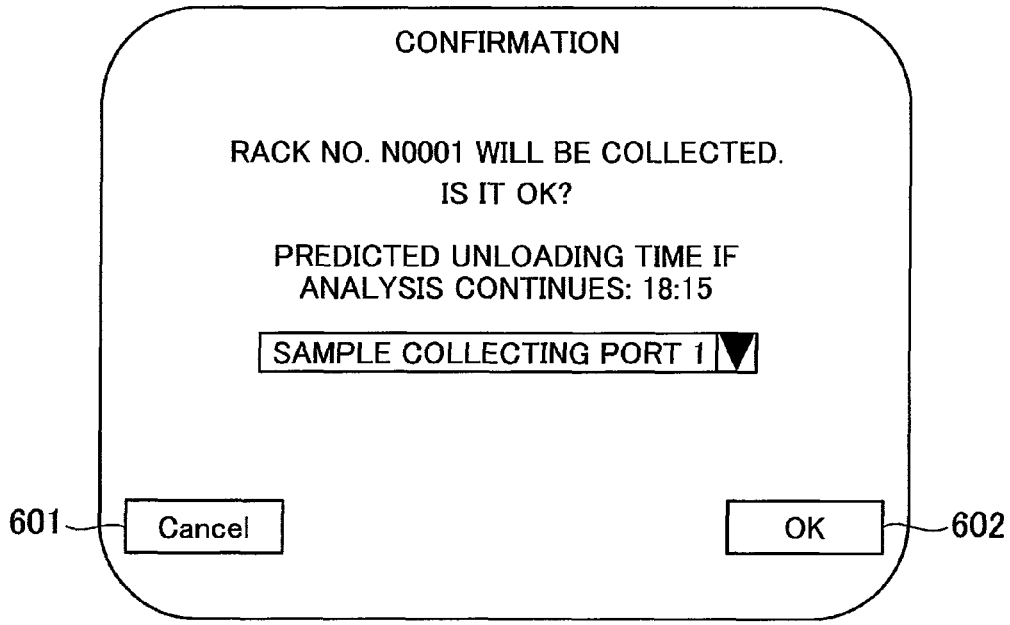
FIG. 14 is an explanatory diagram illustrating means for specifying a sample collecting port according to the embodiment of the present invention.

FIG. 14 is an explanatory diagram illustrating means for specifying a sample collecting port that collects the specified sample and issuing an instruction to collect the sample according to the embodiment of the present invention.

A button 1301 for automatically selecting a collecting port for a general specimen or a button 1302 for manually selecting a collecting port for a general specimen is pressed to set a condition for selecting a collecting port for a general specimen. A button 1303 for automatically selecting a collecting port for an emergent specimen or a button 1304 for manually selecting a collecting port for an emergent specimen is pressed to set a condition for selecting a collecting port for an emergent specimen.

Since a collecting port for a general specimen is automatically or manually selected and set, and a collecting port for an emergent specimen (of which a measurement result needs to be swiftly output) is automatically or manually selected and set, a specimen rack collected according to an instruction (issued by the user) to collect the rack can be identified and extracted so that a specimen can be swiftly remeasured.

When an OK button 1406 is pressed, selected information is stored in collecting port selection condition setting information stored in the storage device included in the whole management computer 9.

In the rack collection schedule generation process of step 205 illustrated in FIG. 2, a collecting port is selected in accordance with the collecting port selection condition setting information stored in the storage device included in the whole management computer 9.

When an automatic selection of a collecting port is specified in the collecting port selection condition setting information, a rack collecting port closest to the halting position of the specimen rack is selected using the rack transport status stored in the storage device included in the whole management computer 9. When the rack collect button illustrated in FIG. 5 is pressed, the confirmation screen illustrated in FIG. 13 is displayed, and the selected rack collecting port is displayed in the sample collecting port select button 1301.

When a manual selection of a collecting port is specified in the collecting port selection condition setting information, and the rack collect button illustrated in FIG. 5 is pressed, the confirmation screen illustrated in FIG. 13 is displayed and a sample collecting port that will collect a sample is specified using the sample collecting port select button 1301.

An OK button 1303 is pressed to instruct the whole management computer 9 to request to collect a rack currently selected using the rack number select button 501.

As described above, according to the present embodiment, even when a specimen needs to be reanalyzed due to an abnormality exists, a rack that holds the specimen can be specified, analysis of the rack can be interrupted, and. The specimen that needs to be reanalyzed due to the abnormality can be reloaded, while it needs not to wait for completion of analysis of another specimen held by the same rack, therefore, it is possible to swiftly obtain a measurement result.

Description Of Reference Numerals
1 Specimen rack loading unit
2 ID reader
3 Transport line
4 Specimen rack standby unit
5, 6, 7 Analyzing module
8 Specimen rack collecting unit
9 Whole management computer
10 Operating unit
11 Display unit

The invention claimed is:

1. An automatic analyzer comprising:
   an analyzing mechanism adapted to analyze biological samples;
   a sample transport device adapted to transport a rack holding a plurality of the biological samples to the analyzing mechanism;
   a sample loading port adapted to load the biological samples onto the sample transport device;
   a sample collecting port adapted to collect the rack so that the rack can be extracted;
   a display unit adapted to selectively display a screen that displays at least information about an analysis status of all biological samples held by the rack which also holds a sample that has an error;
   a specifying mechanism including a specifying button displayed on the screen, the specifying button adapted to specify the sample or the rack so that the sample or the rack that is specified is to be collected by the sample collecting port; and
   a control mechanism adapted to control the sample transport device so that the rack that is specified by the specifying mechanism or holds the sample specified by the specifying mechanism is collected by the sample collecting port.

2. The automatic analyzer according to claim 1, wherein the display unit is adapted to display the samples, of the samples held in the automatic analyzer, that cannot be analyzed for some reason; and the specifying mechanism is adapted to specify a sample, of the samples displayed by the display mechanism, that is collected by the sample collecting port.

3. The automatic analyzer according to claim 2, wherein the display mechanism further displays a reason that the sample cannot be analyzed.

4. The automatic analyzer according to claim 2, wherein the reason that the sample cannot be analyzed includes at least either an error of reading specimen identification information or a sample clogging error.

5. The automatic analyzer according to claim 2, further comprising
a searching mechanism adapted to search the sample, of the samples held in the automatic analyzer, that cannot be analyzed due to a reason.

6. The automatic analyzer according to claim 1, wherein the control mechanism is adapted to control analysis so that scheduled analysis of the sample specified by the specifying mechanism is interrupted and the sample is collected by the sample collecting port.

7. The automatic analyzer according to claim 1, wherein the display mechanism is adapted to display the sample, of the samples collected by the sample collecting port, that needs to be reanalyzed.

8. The automatic analyzer according to claim 1, wherein the display mechanism is adapted to display the fact that the sample specified by the specifying mechanism cannot be collected when the sample specified by the specifying mechanism cannot be collected.

9. The automatic analyzer according to claim 1, wherein the display mechanism is adapted to display an identification of the sample specified by the specifying mechanism.

10. The automatic analyzer according to claim 1, further comprising
a selecting mechanism adapted to select timing of collecting the sample by the sample collecting port, the timing is either:
at the point when the analysis on the sample specified by the specifying mechanism performed by the analyzing mechanism is interrupted; or
at the point when the analysis on the sample being under analyzing upon specified by the specifying mechanism is completed.

11. The automatic analyzer according to claim 1, wherein the display mechanism is adapted to display an error that has occurred; and
the specifying mechanism is adapted to specify a sample incapable of being analyzed due to the error selected from displayed on the displaying mechanism and collected by the sample collecting port.

12. The automatic analyzer according to claim 1, wherein the specifying mechanism is adapted to specify a sample to be collected by the sample collecting port from a high-order analyzing system connected to the automatic analyzer.

13. The automatic analyzer according to claim 1, wherein the specifying mechanism is adapted to specify a sample collecting port that collects the sample.

14. The automatic analyzer according to claim 1, wherein the screen displays a predicted time of when a rack will be stored in the sample collecting port after completion of the analysis of samples held by the rack.

15. An automatic analyzer comprising:
an analyzing mechanism configured to analyze biological samples;
a sample transport device configured to transport a rack holding a plurality of the biological samples to the analyzing mechanism;
a sample loading port configured to load the biological samples onto the sample transport device;
a sample collecting port configured to collect the rack so that the rack can be extracted;
a display unit adapted to selectively display a screen that displays at least information about an analysis status of all biological samples held by the rack which includes a biological sample that has an error;
a controller configured to control the display unit to display a specifying button on the screen to specify that the biological sample that has the error or the rack that holds the biological sample that has the error is to be collected, and, when the specifying button is pressed, to control the sample transport device so that the rack that is specified by the specifying button or holds the biological sample specified by the specifying button is collected by the sample collecting port.

16. The automatic analyzer of claim 15, wherein the control mechanism is configured to control the sample transport device so that the rack that is specified by the specifying button or holds the biological sample specified by the specifying button is collected by the sample collecting port without waiting for analysis of other biological samples held by the rack to complete.

* * * * *